US011517204B2

(12) United States Patent
Ray

(10) Patent No.: US 11,517,204 B2
(45) Date of Patent: Dec. 6, 2022

(54) DETERMINING LVEF USING ELECTROCARDIOGRAPHIC SIGNALS

(71) Applicant: Abhijit Ray, Kolkata (IN)

(72) Inventor: Abhijit Ray, Kolkata (IN)

( * ) Notice: Subject to any disclaimer, the term of this patent is extended or adjusted under 35 U.S.C. 154(b) by 0 days.

(21) Appl. No.: 17/121,052

(22) Filed: Dec. 14, 2020

(65) Prior Publication Data

US 2022/0104711 A1 Apr. 7, 2022

(30) Foreign Application Priority Data

Oct. 1, 2020 (IN) .............................. 202031042747

(51) Int. Cl.
*A61B 5/02* (2006.01)
*A61B 5/353* (2021.01)
*A61B 5/00* (2006.01)
*A61B 5/352* (2021.01)
*A61B 5/355* (2021.01)

(52) U.S. Cl.
CPC .......... *A61B 5/02028* (2013.01); *A61B 5/352* (2021.01); *A61B 5/353* (2021.01); *A61B 5/355* (2021.01); *A61B 5/746* (2013.01)

(58) Field of Classification Search
None
See application file for complete search history.

(56) References Cited

U.S. PATENT DOCUMENTS

| 4,294,259 A | * | 10/1981 | Picunko | A61B 6/507 600/431 |
| 5,161,539 A | * | 11/1992 | Evans | A61B 5/282 600/513 |

FOREIGN PATENT DOCUMENTS

RU 2646749 C9 3/2018
WO 2018195058 A1 10/2018

OTHER PUBLICATIONS

Indian Patent Office, Examination Report in Application No. 202031042747 under sections 12 and 13 of the Patents Act, 1970 and the Patent Rules 2003, Intellectual Property India, Apr. 29, 2022. pp. 1-6.
Line Lisbeth Olesen and Andreas Andersen, ECG as a first step in the detection of left ventricular systolic dysfunction in the elderly, ESC Heart Fail. Mar. 2016; 3(1): 44-52. Published online Oct. 30, 2015. doi: 10.1002/ehf2.12067.

* cited by examiner

*Primary Examiner* — Catherine M Voorhees
*Assistant Examiner* — Roland Dinga
(74) *Attorney, Agent, or Firm* — Yantra Patents LLC; Anand P. Narayan

(57) ABSTRACT

Described herein is a computer implemented method of measuring the determining the Left Ventricular Ejection Fraction (LVEF) of a patient. The S Wave, P Wave, R Wave and T Wave are continually measured using an ECG apparatus. The LVEF is computed as a function of S Wave, P Wave, R Wave and T Wave. The system described herein includes an ECG apparatus and an analytical computing device for computing the LVEF.

7 Claims, 6 Drawing Sheets

DETERMINING LVEF USING ELECTROCARDIOGRAPHIC SIGNALS

TECHNICAL FIELD OF THE INVENTION

This invention in general relates to a method and apparatus for determining Left Ventricular Ejection Fraction (LVEF), and specifically to the measurement of LVEF using electrocardiographic (EKG) signals.

BACKGROUND

According to the American Heart Association, Left Ventricular Ejection Fraction (LVEF) is defined as the measurement, expressed as a percentage, of how much blood the left ventricle pumps out with each contraction. It is the most common method for assessment of systolic function.

LVEF measurement is one of the hallmarks in diagnosis and prognosis of heart failure patients. In many cardiology emergencies such as Acute Myocardial Infarction and acute Congestive Cardiac Failure, there is an urgency to measure the LVEF since treatment plans often depend on it.

At present, the standard method of assessing LVEF is by conducting an Echocardiography, using the modified Quinones Equation. Hence, LVEF can only be assessed as snapshots rather than as a continuous parameter.

LVEF can be determined using several invasive and non-invasive imaging modalities, either subjectively by visual estimation or objectively by quantitative methods i.e., echocardiography, magnetic resonance imaging (MRI), computed tomography (CT), gated equilibrium radionuclide angiography (commonly referred to as multiple-gated acquisition [MUGA] scan) and gated myocardial perfusion imaging with either single-photon emission computed tomography (SPECT) or positron emission tomography (PET). LVEF can also be measured non-invasively using the 'first-pass' radionuclide technique, but this technique is rarely performed in the current era. However, none of these have the advantage of continuous monitoring. Also, the above mentioned are much more expensive than ECG and require trained professionals, whereas ECG lead placements require very basic training. In this application, the abbreviations ECG and EKG are used interchangeably, and both refer to electrocardiography. The abbreviations vary across different countries, but universally have the same meaning.

SUMMARY OF THE INVENTION

Many factors affect LVEF such as sympathetic stimulation, blood volume and respiration. Due to these factors, LVEF is a dynamic measurement and hence continuous monitoring will provide more information regarding the patient's condition rather than a snapshot in a limited window of time.

The invention disclosed herein, which determines the LVEF (Left Ventricular Ejection Fraction) from ECG (Electrocardiography) instead of the conventional echocardiography, has the following advantages.

Advantageously, LVEF is continuously measured.

Advantageously, LVEF monitoring conducted through ECG instead of the conventional echocardiography is more economical.

Advantageously, LVEF monitoring requires no additional instruments other than the ECG with an analytical computing device.

Advantageously, the patient's position is not important during LVEF measurement. Trained personnel are required only during placement of leads, whereas echocardiography requires doctor/technician's constant presence during the procedure.

Advantageously, ambulatory leads can be used to measure LVEF during daily activities. In the proposed ECG based LVEF solution, once the leads are placed, it automatically records the ECG readings on paper/monitor; hence can be used continuously to assess patients and collect data. Whereas, in conventional echocardiography, since a doctor/technician is required throughout the procedure, the procedure cannot be conducted for a long period. Hence only snapshots of data are available in convention echocardiography.

In the proposed ECG based LVEF solution, automatic monitoring of LVEF will involve a continuous display of LVEF values throughout the day, and if the LVEF becomes too low, automatically an alarm can be set-off. Whereas, in conventional echocardiography, in case of any acute emergencies such as very low LVEF, the person operating the echo has to notify the concerned nurse/doctor in person.

BRIEF DESCRIPTION OF THE DRAWINGS

The foregoing summary, as well as the following detailed description of the invention, is better understood when read in conjunction with the appended drawings. For illustrating the invention, exemplary constructions of the invention are shown in the drawings. However, the invention is not limited to the specific components disclosed herein. The description of a component referenced by a numeral in a drawing is applicable to the description of that component shown by that same numeral in any subsequent drawing herein.

DETAILED DESCRIPTION OF THE INVENTION

The presently disclosed subject matter now will be described more fully hereinafter with reference to the accompanying Figures, in which some, but not all embodiments of the inventions are shown. Like numbers refer to like elements throughout. The presently disclosed Subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Left Ventricular Ejection Fraction (LVEF) is defined as the percentage of blood pumped out of the left ventricle of the heart with each contraction.

Stroke Volume is defined as the amount of blood pumped out of the left ventricle with each contraction. Ventricular contraction, also called ventricular systole has two major phases in the cardiac cycle—Isovolumetric Contraction and Ejection phases. Since the Aortic valve is not open during the Isovolumetric Contraction phase of Ventricular Systole, this phase is not taken into calculation since pumping out of blood i.e. Stroke Volume can only be possible when Aortic valve is open. Again, the rapid increase in ventricular pressure during systole comes back to baseline during the 1st phase of Ventricular Diastole, which is the Isovolumetric Relaxation phase. Also, a small amount of blood re-enters the ventricles because of valve closure in this phase and hence Isovolumetric Relaxation phase of the cardiac cycle is important while measuring Stroke Volume.

Thus, in the cardiac cycle, we concentrate on the duration from start of Ejection phase to end of Isovolumetric Relaxation phase.

Figure 3:
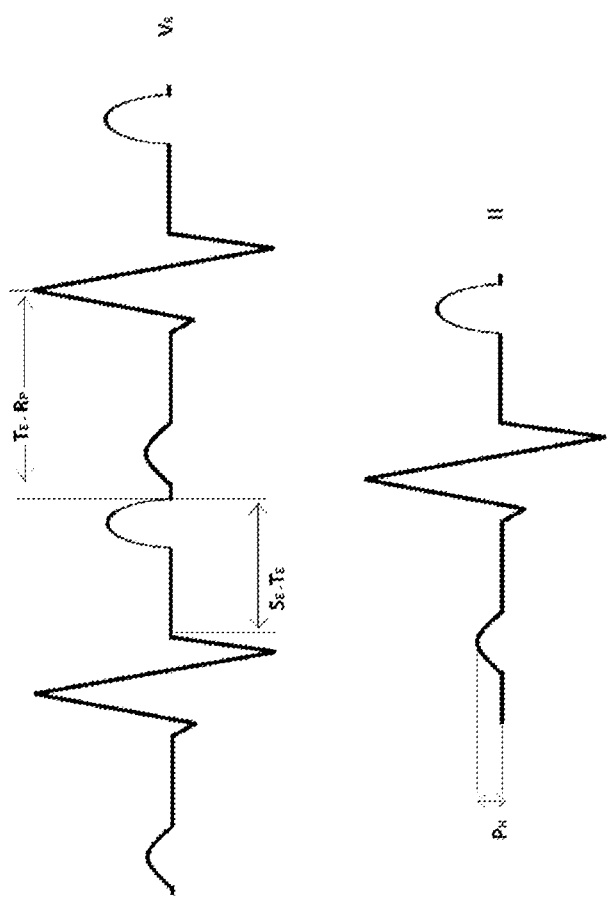
FIG. 3 illustrates the variables measured to compute LVEF in an ECG graph, per techniques of this disclosure.

FIG. 3 illustrates the variables measured to compute LVEF in an ECG graph.

P wave is defined as the small positive deflection from the isoelectric baseline at the start of each cardiac cycle in an ECG which corresponds to the atrial depolarization. R wave is the first positive deflection after the P wave. It represents early ventricular depolarization. S wave is the negative deflection immediately following the R wave. S wave represents depolarization of Purkinje fibres. T wave follows the QRS complex and represents ventricular depolarization. Though typically a positive wave, the T wave can have various morphologies indicating benign or clinically significant myocardial injury.

Figure 4:
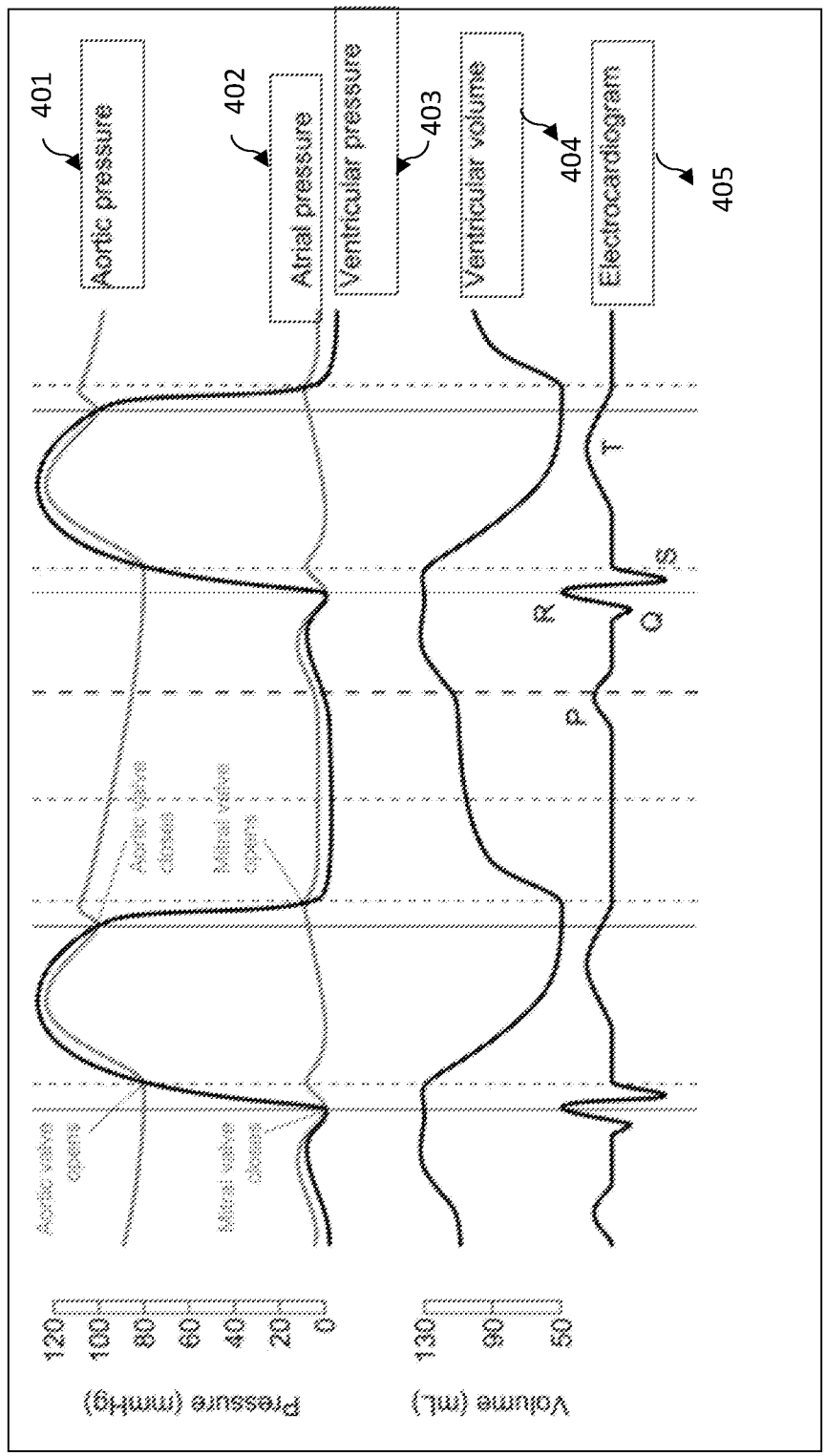
FIG. 4 illustrates the Wiggers diagram, per techniques of this disclosure.

FIG. 4. is Wigger's diagram that illustrates the relationship between the ECG, the pressure, and volume changes in the aorta and left ventricle. The X-axis is a plot of time, and the Y-axis plot is a relationship comparison of Aortic pressure 401, Atrial pressure 402, Ventricular pressure 403, ventricular volume 404 and Electrocardiogram 405.

From Wigger's Diagram; duration, when plotted against an ECG, starts at the end of S wave (SE) and continues till the end of T wave (TE).

The End Diastolic Volume is defined as the amount of blood in the left ventricle just before ventricular contraction. This blood accumulates in the left ventricle over two major phases of the cardiac cycle—Ventricular Filling phase (also called Rapid Inflow) and the beginning of Atrial Systole.

Since the focus is on the left ventricle, all the waves and intervals shall be measured in V6 lead of a standard 12 lead ECG, while P wave is best observed in lead II, only PH shall be measured in lead II.

Figure 1:
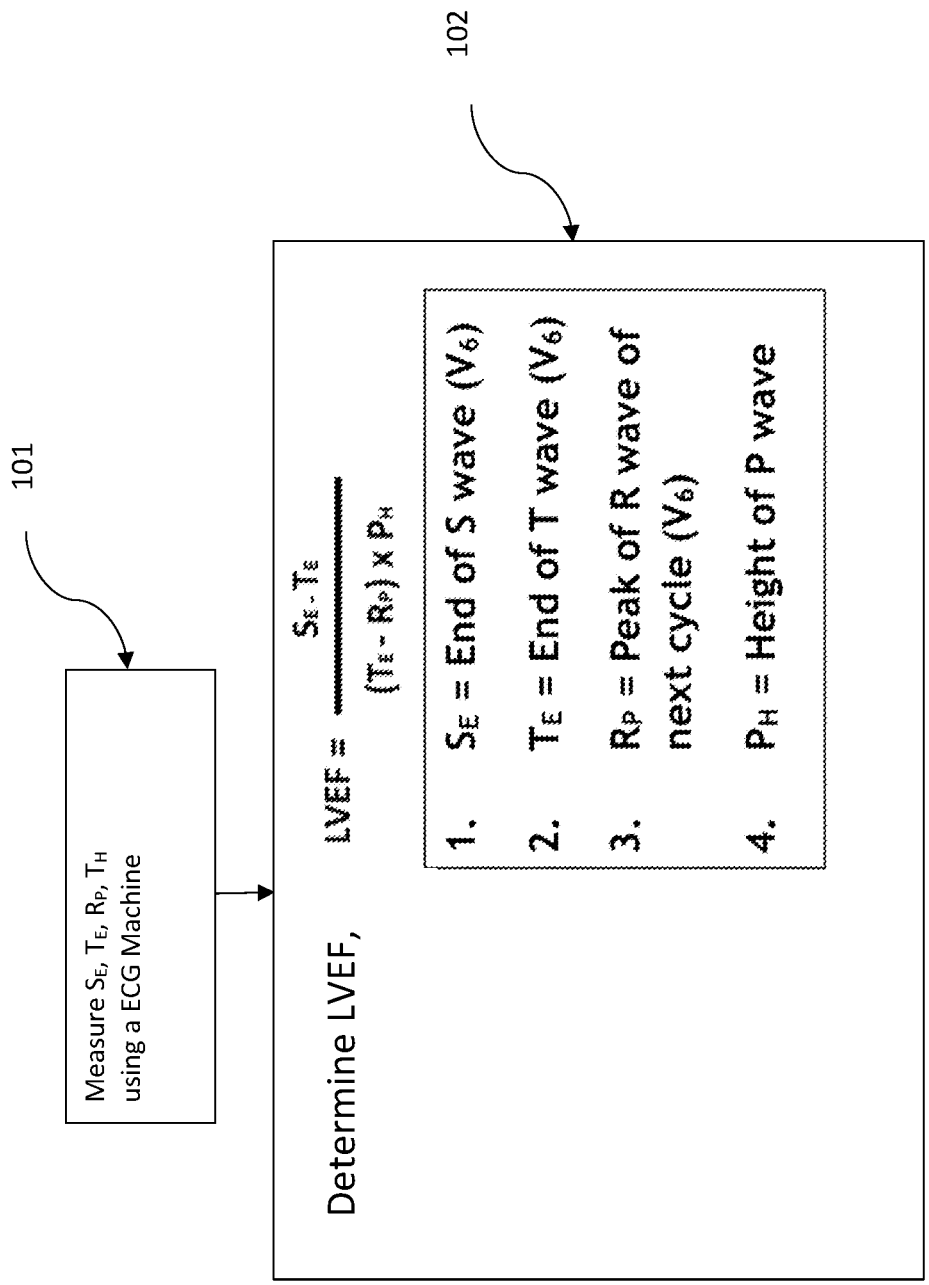
FIG. 1 illustrates a computer implemented method of calculating LVEF, per techniques of this disclosure.

FIG. 1 illustrates the computer implemented method of calculating LVEF.

Figure 2:
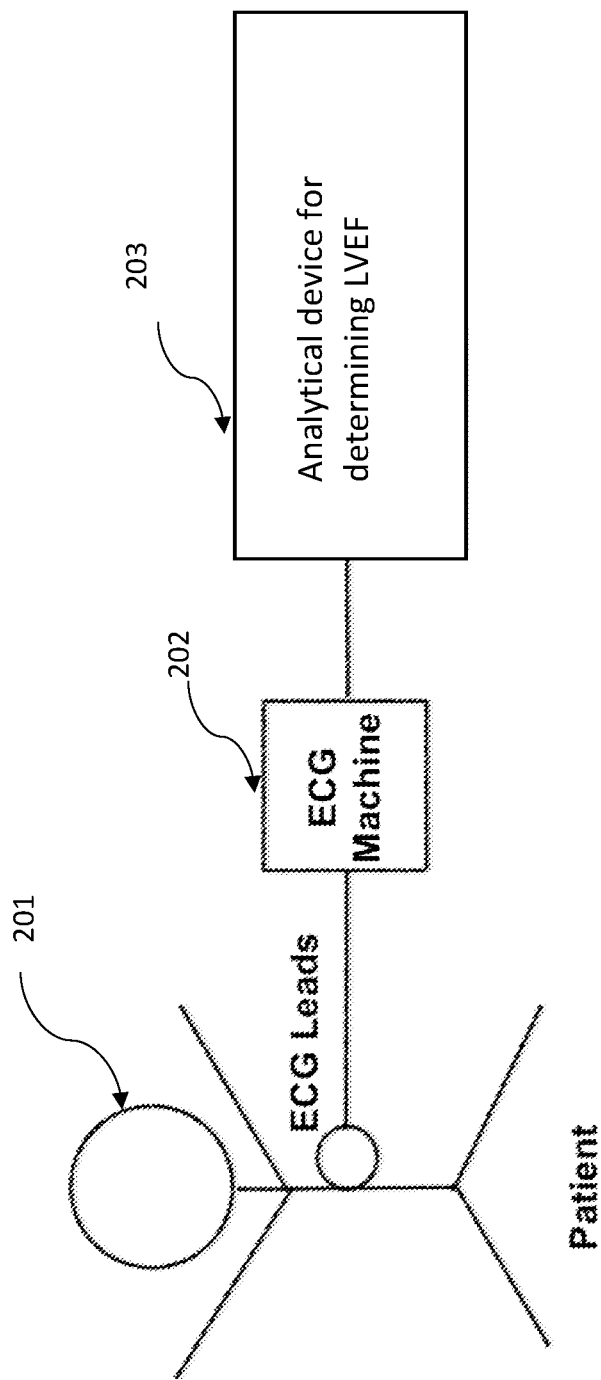
FIG. 2 illustrates a system applied for computing LVEF, per techniques of this disclosure.

Described herein is a computer implemented method of measuring the LVEF of a patient. The S Wave, P Wave, R Wave, and T Wave are measured 101 using an ECG apparatus 202, as depicted in FIG. 2.

The LVEF is computed 102 by applying the S Wave, P Wave, R Wave and T Wave in an equation as follows;

$$LVEF = \frac{(S_E - T_E)}{(T_E - R_P) \times P_H}$$

The qualitative logic for the above formula is described hereafter. Left Ventricular Ejection Fraction (LVEF) is defined as the percentage of blood pumped out of the left ventricle of the heart with each contraction. It is measured by dividing Stroke Volume by End-Diastolic Volume.

Stroke Volume is defined as the amount of blood pumped out of the left ventricle with each contraction. Ventricular contraction, also called ventricular systole has two major phases in the cardiac cycle—Isovolumetric Contraction and Ejection phases. Since the Aortic valve is not open during the Isovolumetric Contraction phase of Ventricular Systole, this phase is not taken into calculation since pumping out of blood i.e. Stroke Volume can only be possible when Aortic valve is open. Again, the rapid increase in ventricular pressure during systole comes back to baseline during the 1st phase of Ventricular Diastole, which is the Isovolumetric Relaxation phase. Also, a small amount of blood re-enters the ventricles because of valve closure in this phase; and hence Isovolumetric Relaxation phase of the cardiac cycle is important while measuring Stroke Volume. Thus in the cardiac cycle, the focus is on the duration from start of Ejection phase to end of Isovolumetric Relaxation phase. From Wigger's Diagram, we know that this duration, when plotted against an ECG, starts at the end of S wave (SE) and continues till the end of T wave (TE).

So the numerator of the invented formula is $S_E$ to $T_E$, i.e. $(S_E-T_E)$

End Diastolic Volume is defined as the amount of blood in the left ventricle just before ventricular contraction. This blood accumulates in the left ventricle over two major phases of the cardiac cycle—Ventricular Filling phase (also called Rapid Inflow) and the beginning of Atrial Systole. From the Wigger's diagram, we see that the time from Ventricular Filling phase to Atrial Systole coincides with end of T wave (TE) to the peak of R wave of the next cycle (RP). Now both the T wave and the QRS complex give information regarding ventricular events. However, to accommodate Atrial Systole, which is the contraction of the Left Atrium to pump blood into the Left Ventricle, this must be multiplied with the height of P wave (PH) since only the P wave in an ECG gives us data from the atria. Hence, the denominator of the of the LVEF computation is $(T_E-R_p) \times P_H$ FIG. 2 illustrates the system applied for computing LVEF. ECG Leads are attached to the patient 201, ECG parameters are recorded, analyzed by a computing device 203 and the LVEF results are presented in a user readable format. The LVEF measurements are conducted over a period of time. The LVEF computed shown above requires ECG data from any two successive cardiac cycles. Hence, a two-cycle length is enough to determine the LVEF from this formula, irrespective of the time taken to complete these two cycles. Time will be reduced in any tachycardia and increased in any bradycardia. If the ECG leads are kept attached to the patient, LVEF can be measured continuously.

The various waves of an ECG usually have the same dimensions and inter-wave relationships between each other and hence LVEF will remain constant. However, in various arrhythmias, the heart rate and rhythm may keep on changing.

Even in these cases, the LVEF can be continuously measured from the previous two cycle lengths. Hence, irrespective of the diagnosis, LVEF can be measured from formula (1) for as long as required, there is no upper limit for the time frame. The minimum time required to obtain a result is two cardiac cycles. In normal patients with a heart rate between 60 and 100 beats per minute, two cycles will be obtained within 2 to 3.3 seconds.

The most common and important function of LVEF measurement is to diagnose patients with heart failure. Not only diagnosis, even the prognosis can be predicted to some extent from LVEF measurements alone. Though some causes of Heart Failure are reversible, most causes of Heart Failure involve an irreversible process which can only be halted but never fully cured. To assess the degree of damage the pathology has done to the cardiac muscle, LVEF is one of the most important criteria and correlated with the clinical symptoms to assess the patient's status. Exemplarily, for normal healthy individuals, LVEF is typically in the about 50% to about 70% range. For patients with Dyspnea on Exertion, i.e. in the borderline case LVEF is typically in the range about 41% to about 49%. For patients wherein Dyspnea may even occur at rest, i.e. in the heart failure and high risk case, LVEF is typically less than about 40%.

FIG. 2 illustrates the system applied for computing LVEF. The LVEF measurement system, comprises an ECG measuring apparatus 202 that obtains orthogonal ECG measurements of S Wave, P Wave, R Wave and T Wave of a patient 201. It also comprises an analytical computing device 203 operatively connected to the ECG measuring equipment 202 that receives the ECG measurements of S Wave, P Wave, R Wave and T Wave, and computes the LVEF. The ECG measuring apparatus 202 includes leads and a surface monitoring device.

The ECG machine 202 consists of electrodes, connecting wires, an amplifier, and a storage and transmission device. The electrodes, or leads, used in an ECG machine can be divided into two types, bipolar and unipolar. The bipolar limb leads are used to record the voltage differential between the wrists and the legs. These electrodes are placed on the left leg, the right wrist, and the left wrist of the patient 201, forming a triangular movement of the electrical impulse in the heart that can then be recorded. Unlike bipolar leads, unipolar leads record the voltage difference between a reference electrode and the body surface to which they are attached. These electrodes are attached to the right and left arms and the right and left legs. Additionally, they are placed at specific areas on the chest and are used to view the changing pattern of the heart's electrical activity.

Various models of electrodes are made, including plate, suction, fluid column, and flexible, among others. Plate electrodes are metal disks which are constructed out of stainless steel, German silver, or nickel. They are held onto the skin with adhesive tape. Suction electrodes use a vacuum system to remain in place. They are designed out of nickel or silver and silver chloride and are attached to a compressor that creates the vacuum. Another type of electrode, the fluid column electrode, is less sensitive to patient movement because it is designed to avoid direct contact with the skin. The flexible electrode is most useful for taking ECG readings in infants. It is a mesh woven from fine stainless steel or silver wire with a flexible lead wire attached. The electrode attaches to the skin like a small bandage.

ECG amplifiers are needed to convert the weak electrical signal from the body into a more readable signal for the output device. A differential amplifier is useful when measuring relatively low level signals. During an ECG, the electrical signal from the body is transferred from the electrodes to the first section of the amplifier, the buffer amplifier. Here the signal is stabilized and amplified by a factor of five to 10. An electronic network follows, and the signal from the unipolar leads is translated. A differential pre-amplifier then filters and amplifies the signal by a factor of 10 to 100.

The sections of the amplifier which receive direct signals from the patient are separated from the main power circuitry of the rest of the ECG machine 202 by optical isolators, preventing the possibility of accidental electric shock. The primary amplifier is found in the main power circuitry. In this powered amplifier, the signal is converted to a current suitable for output to the appropriate device.

The most common form of output for ECG machines 202 is a paper-strip recorder. This device provide a hard copy of the ECG signal over time. Many other types of devices are also used, including computers, oscilloscopes, and magnetic tape units. Since the data collected is in analog form, it must be converted to digital form for use by most electronic output devices. For this reason the primary circuitry of the ECG typically has a built-in analog to digital converter section.

Various other parts are needed to complete the ECG unit 202. Since the signal is weakly transmitted through the skin to the electrodes, an electrolyte paste is usually used. This paste is applied directly to the skin. It is composed primarily of chloride ions which help form a conductive bridge between the skin and the electrode, allowing better signal transmission. Other components include mounting clips, various sensors, and thermal papers.

Figure 5:
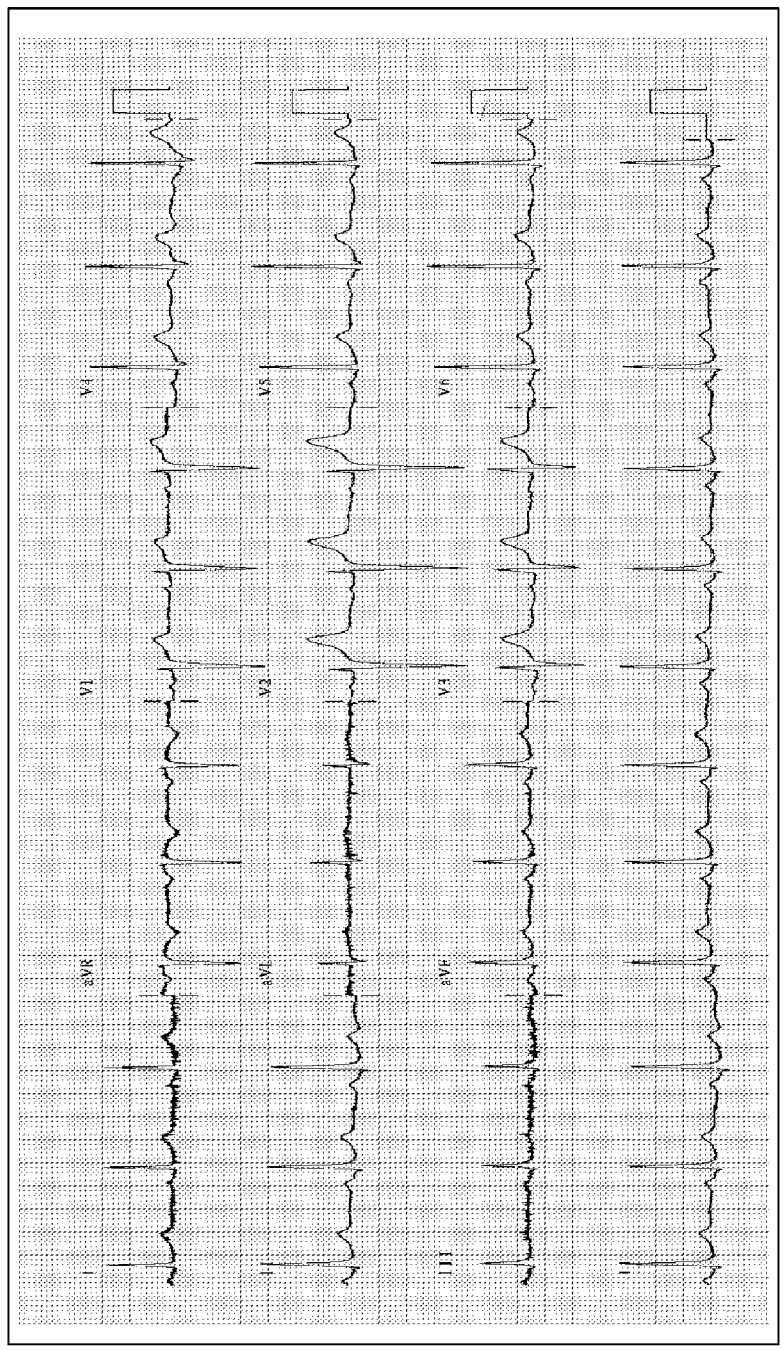
FIG. 5 illustrates graphically a first example comparing the LVEF calculation of the invention described herein vs the LVEF reported by echocardiography, per techniques of this disclosure.

FIG. 5 illustrates graphically a first example comparing the LVEF calculation of the invention described herein vs the LVEF reported by echocardiography. The LVEF determined through the method and system disclosed herein (77%) equates closely to the LVEF measured (78%) through conventional echocardiography.

Figure 6:
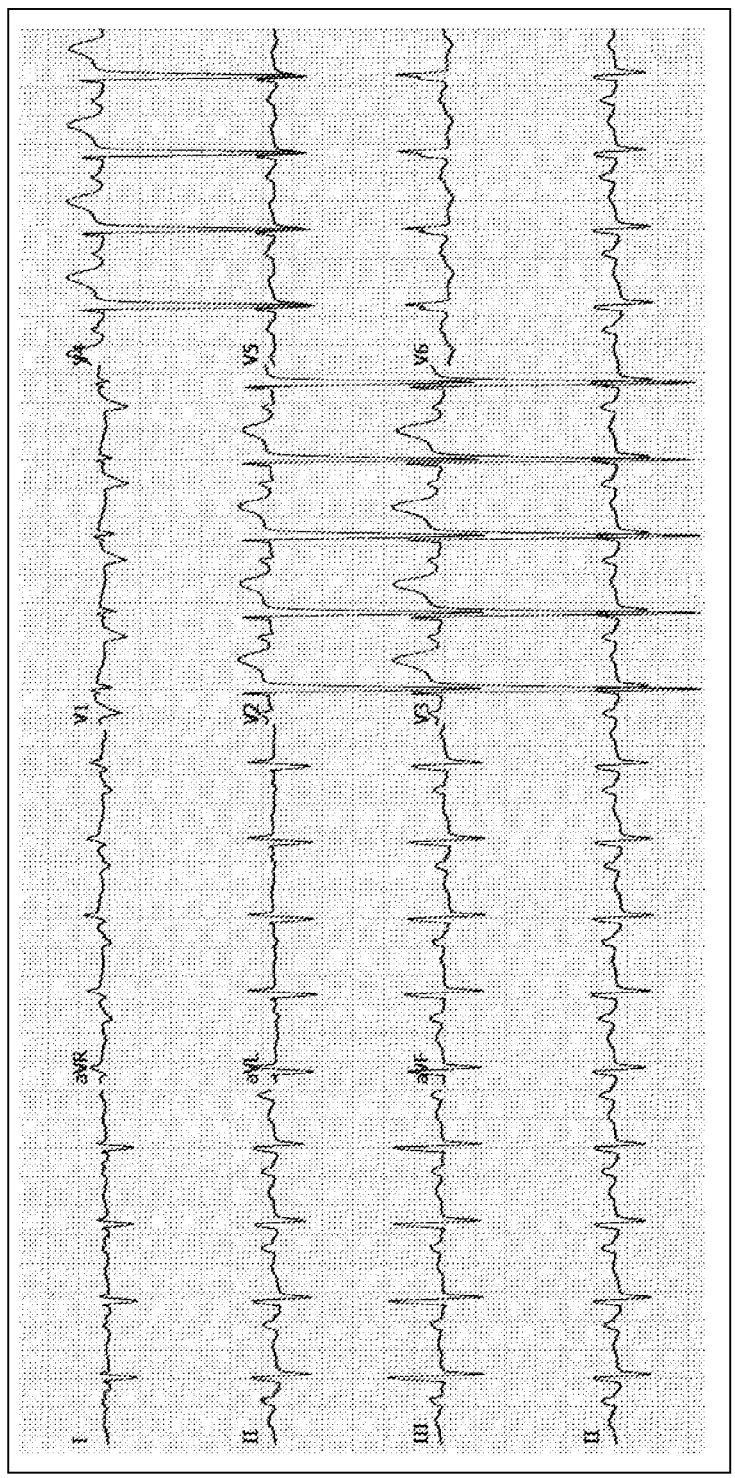
FIG. 6 illustrates graphically a second example comparing the LVEF calculation of the invention described herein vs the LVEF reported by echocardiography, per techniques of this disclosure.

FIG. 6 illustrates graphically a second example comparing the LVEF calculation of the invention described herein vs the LVEF reported by echocardiography. The LVEF determined through the method and system disclosed herein (62%) equates closely to the LVEF measured (61%) through conventional echocardiography.

The foregoing examples have been provided merely for explanation and are in no way to be construed as limiting of LVEF monitoring system and method disclosed herein. While the LVEF monitoring system and method has been described with reference to particular embodiments, it is understood that the words, which have been used herein, are words of description and illustration, rather than words of limitation. Furthermore, although the LVEF monitoring system and method has been described herein with reference to particular means, materials, and embodiments, the LVEF monitoring system and method is not intended to be limited to the particulars disclosed herein; rather, the design and functionality of the LVEF monitoring system and method extends to all functionally equivalent methods, structures and uses, such as are within the scope of the appended claims. While particular embodiments are disclosed, it will be understood by those skilled in the art, having the benefit of the teachings of this specification, that the LVEF monitoring system and method disclosed herein is capable of modifications and other embodiments may be effected and changes may be made thereto, without departing from the scope and spirit of the LVEF monitoring system and method disclosed herein.

What is claimed is:

1. A computer implemented method of dynamically and continually measuring Left Ventricular Ejection Fraction (LVEF) of a patient, and diagnosing a level of health risk, comprising the steps of:
measuring S Wave, P Wave, R Wave, and T Wave using an electrocardiography (ECG) apparatus by placing electrodes on a leg and wrist of the patient;
dynamically and continually computing using an analytical computing device the LVEF by applying said S Wave, P Wave, R Wave, and T Wave as follows $$LVEF = \frac{(S_E - T_E)}{(T_E - R_p) \times P_H};$$

and wherein,
$T_E$ is an end of the T Wave, and wherein the T wave represents ventricular depolarization;
$R_P$ is a peak of the R Wave of a next cycle, and wherein the R wave is a first positive deflection after P wave;
$S_E$ is an end of the S Wave, and wherein the S wave is a negative deflection immediately following the R wave;
$P_H$ is height of the P wave, and wherein the P wave is a small positive deflection from an isoelectric baseline at a start of each cardiac cycle in an ECG which corresponds to atrial depolarization;
presenting said LVEF results in a user readable format on a monitor; and
diagnosing said patient as a normal healthy individual, borderline risk, or high risk case based on said computed LVEF.

2. The method of claim 1, wherein a patient is diagnosed as a normal healthy individual for the LVEF in the 50% to 70% range, diagnosed as a borderline risk case for the LVEF in the range of 41% to 49%, and diagnosed as a high risk case when the LVEF is less than 40%.

3. A Left Ventricular Ejection Fraction (LVEF) measurement system for dynamically and continually measuring LVEF of a patient, and diagnosing level of health risk, comprising:
an electrocardiography (ECG) measuring apparatus that obtains orthogonal ECG measurements of S Wave, P Wave, R Wave, and T Wave, further comprising electrodes, that are placed on a leg and wrist of the patient; and
an analytical computing device operatively connected to the ECG measuring apparatus that receives said ECG measurements of S Wave, P Wave, R Wave, and T Wave, and dynamically and continually computes the LVEF results as follows:

$$LVEF = \frac{(S_E - T_E)}{(T_E - R_p) \times P_H}$$

wherein
$T_E$ is an end of the T Wave, and wherein T wave represents ventricular depolarization;
$R_P$ is a peak of the R Wave of a next cycle, and wherein the R wave is a first positive deflection after P wave;
$S_E$ is an end of the S Wave, and wherein the S wave is a negative deflection immediately following the R wave;
$P_H$ is a height of the P wave, and wherein the P wave is a small positive deflection from an isoelectric baseline at a start of each cardiac cycle in an ECG which corresponds to atrial depolarization; and
said analytical computing device presents said LVEF results in a user readable format on a monitor and diagnoses said patient as a normal healthy individual, borderline risk, or high risk case based on said computed LVEF results.

4. The LVEF measurement system of claim 3, wherein all the waves and intervals are measured in V6 lead of a standard 12 lead ECG.

5. The LVEF measurement system of claim 3, wherein P wave is observed in lead II, and only PH is be measured in lead II.

6. The LVEF measurement system of claim 3, wherein said ECG measuring apparatus includes leads and a surface monitoring device.

7. The LVEF measurement system of claim 3, further comprising an alarm when LVEF falls below predetermined limits.

* * * * *